(12) United States Patent
Rokosz et al.

(10) Patent No.: US 8,968,227 B2
(45) Date of Patent: Mar. 3, 2015

(54) KNEE BRACE

(75) Inventors: John A. Rokosz, Belmont, MA (US);
Philip P. Carvey, Bedford, MA (US);
Nicholas S. Howard, Bedford, MA (US); Andrew W. Carvey, Cambridge, MA (US); Matthew R. Carvey, Somerville, MA (US)

(73) Assignee: Adicep Technologies, Inc., Bedford, MA (US)

( * ) Notice: Subject to any disclaimer, the term of this patent is extended or adjusted under 35 U.S.C. 154(b) by 142 days.

(21) Appl. No.: 13/355,604

(22) Filed: Jan. 23, 2012

(65) Prior Publication Data

US 2013/0190669 A1 Jul. 25, 2013

(51) Int. Cl.
*A61F 5/00* (2006.01)
*A61H 5/00* (2006.01)
*A61F 2/64* (2006.01)

(52) U.S. Cl.
USPC .................................. 602/16; 601/35; 623/42

(58) Field of Classification Search
USPC .............. 602/5, 1, 16, 23, 26; 623/27, 38–53; 601/5, 23, 24, 26, 27, 33–35
See application file for complete search history.

(56) References Cited

U.S. PATENT DOCUMENTS

| | | |
|---|---|---|
| 2,010,482 A | 8/1935 | Cobb |
| 2,632,440 A | 3/1953 | Hauser et al. |
| 3,315,406 A | 4/1967 | Ryan |
| 4,413,713 A | 11/1983 | West |
| 4,771,872 A | 9/1988 | Kampf |
| 5,011,136 A | 4/1991 | Rennex |
| 5,052,379 A | 10/1991 | Airy et al. |
| 5,230,700 A | 7/1993 | Humbert et al. |
| 5,476,441 A | 12/1995 | Durfee et al. |
| 5,558,627 A | 9/1996 | Singer et al. |
| 5,575,764 A | 11/1996 | Van Dyne |
| 5,636,805 A | 6/1997 | Fukuzawa |
| 5,830,166 A | 11/1998 | Klopf |
| 6,010,474 A | 1/2000 | Wycoki |
| 6,024,713 A | 2/2000 | Barney |
| 6,471,664 B1 | 10/2002 | Campbell et al. |
| 6,500,138 B1 * | 12/2002 | Irby et al. .......... 602/26 |
| 6,527,733 B1 | 3/2003 | Ceriani et al. |
| 6,666,796 B1 | 12/2003 | MacCready |
| 6,834,752 B2 * | 12/2004 | Irby et al. .................. 192/81 C |
| 7,153,242 B2 | 12/2006 | Goffer |
| 7,306,572 B2 | 12/2007 | Ceriani et al. |
| 7,393,335 B2 * | 7/2008 | Carvey et al. ................... 602/26 |
| 7,608,051 B1 | 10/2009 | Nace |

(Continued)

FOREIGN PATENT DOCUMENTS

DE 44 00 820 1/1994
EP 1229874 B1 7/2007

(Continued)

*Primary Examiner* — Alireza Nia
*Assistant Examiner* — Tarla Patel
(74) *Attorney, Agent, or Firm* — The Patent Practice of Szmanda & Shelnut, LLC; Charles R. Szmanda; James G. Shelnut

(57) ABSTRACT

Disclosed and claimed herein is an improved leg brace having a thigh frame, a shank frame, a knee assembly rotatably coupling the thigh frame to the shank frame, and a shoe component attached to the shank frame; the knee assembly having a spring, clutch, means for engaging the clutch; and programmable means for engaging the clutch at a selected angle between the thigh frame and shank frame.

15 Claims, 8 Drawing Sheets

(56) References Cited

U.S. PATENT DOCUMENTS

| | | |
|---|---|---|
| 7,850,632 B2 | 12/2010 | Gilmour |
| 8,057,414 B2 | 11/2011 | Nace |
| 2002/0094919 A1 | 7/2002 | Rennex et al. |
| 2003/0062241 A1 | 4/2003 | Irby et al. |
| 2003/0149386 A1 | 8/2003 | Ceriani et al. |
| 2004/0267179 A1 | 12/2004 | Lerman |
| 2007/0100265 A1 | 5/2007 | Gamada |
| 2007/0232972 A1 | 10/2007 | Martinez |
| 2008/0188784 A1 | 8/2008 | Ceriani et al. |
| 2009/0036804 A1* | 2/2009 | Horst ................................ 601/5 |
| 2010/0106065 A1 | 4/2010 | Ward |
| 2011/0152736 A1 | 6/2011 | Ng |

FOREIGN PATENT DOCUMENTS

| | | |
|---|---|---|
| EP | 1829507 A1 | 9/2007 |
| EP | 2316393 A1 | 5/2011 |
| WO | WO 94/09727 | 5/1994 |

* cited by examiner

A

B

C

KNEE BRACE

FIELD OF THE INVENTION

The present invention relates to orthopedic braces that are fitted to a patient's leg, knee and foot.

BACKGROUND

In patients with knee osteoarthritis, as the tibiofemoral forces increase, knee pain can increase significantly. It is therefore of value to reduce the tibiofemoral forces on the knee joint during ambulation over a variety of surfaces and terrains.

A number of orthotic devices have been designed to reduce tibiofemoral joint forces and alleviate pain associated with joint movement, and sometimes to rehabilitate the joint over time.

For example, Nace, in U.S. Pat. No. 8,057,414 discloses and claims an offloading brace that is designed to relieve pressure on either the medial or lateral side of the tibiofemoral joint. In addition, there is employed a "spring loaded adjustable fulcrum" to assist in leg extension after the knee is flexed. However, while different amounts of spring torque may be introduced by adjusting the mechanical spring settings before the brace is donned, there are no means for modifying the spring torque while being worn or programmably as a function of knee angle. Moreover, there are no means for locking the spring in compression and releasing the spring at a selected angle during ambulation.

As a further example, in U.S. Pat. No. 6,010,474, Wycoki discloses a leg orthotic device that is said to offload tibiofemoral forces on the knee joint bilaterally. In addition, the disclosed orthotic device is said to relieve pressure on the patellar compartment. There is also disclosed a spring assembly for "biasing the knee toward extension." The pressure on the knee joint is said to be offloaded by "transferring the pressure through the strut assembly to the thigh" using straps and an inflatable thigh cuff. However, while different amounts of spring thrust at heel strike may be introduced by adjusting the mechanical spring settings before the brace is donned, there are no means for modifying the spring thrust while being worn or programmably as a function of knee angle. Moreover, there are no means for locking the spring in compression and releasing the spring at a selected angle during ambulation.

In U.S. Pat. No. 7,393,335, Carvey et al., incorporated herein by reference, disclose a knee brace that provides support for the torso via the hip and increases leg thrust. However, Carvey et al. do not provide a method of programmably modifying the torque from the spring beginning at a programmable angle during knee flexion and releasing the spring at a programmable angle during knee extension.

Therefore, there remains a need for a biomechanical leg orthosis that, during ambulation, provides a programmable means for storing energy while the knee is flexing and a means for programmably releasing the stored energy when the knee is extending. Moreover, there remains a need for an improved leg orthosis that begins storing energy at a selected angle of knee flexion angle after heel strike. These needs are addressed by the subject matter disclosed and claimed herein.

DETAILED DESCRIPTION

As used herein, the conjunction "and" is intended to be inclusive and the conjunction "or" is not intended to be exclusive unless otherwise indicated. For example, the phrase "or, alternatively" is intended to be exclusive. As used herein, the article "a" is understood to mean "one or more." As used herein, the term "exemplary" is understood to indicate a particular example and is not otherwise intended to indicate preference. As used herein, the "knee angle" is understood to be measured by using the angle between the thigh frame and the shank frame of the leg brace in circumstances where the leg brace is being worn. Herein, "knee flexion" is understood as the act of bending the knee joint. Herein, "knee extension" is understood as the act of straightening the knee joint. It is further understood that the knee joint can be hyperextended beyond its normal straightened position.

Disclosed and claimed herein is an improved leg brace having a thigh frame, a shank frame, a knee assembly rotatably coupling the thigh frame to the shank frame, and a shoe component attached to the shank frame; the knee assembly having a spring, a clutch, and means for engaging the clutch; the improvement comprising: programmable means for engaging the clutch at a selected angle between the thigh frame and shank frame.

Further disclosed and claimed herein is a leg brace, having: a shank frame for transferring forces between a wearer's tibia/fibula and the shank frame; a thigh frame for transferring forces between a wearer's femur and the thigh frame; at least one knee joint for rotatably coupling the shank frame to the thigh frame; at least one non-linear torsion spring having a torsional axis at the at least one knee joint wherein the torsion spring hardens with increasing angle of knee flexion; at least one clutch with an input arbor coupled to the at least one non-linear torsion spring and an output arbor coupled to the thigh frame or the shank frame; a programmable controller, operatively coupled to the at least one clutch, for engaging the at least one clutch at a selected angle in relation to the heel strike during ambulation, whereby a reduction of tibiofemoral forces results; and releasing the at least one clutch at a selected angle during knee extension.

The leg brace disclosed and claimed herein may further comprise a second knee assembly, configured so that, when in use, one knee assembly is on the medial side of the leg and the other knee assembly is on the lateral side of the leg. This arrangement may be particularly useful in situations where bicompartmental relief of pressure on the tibiofemoral joint is desired.

The leg brace disclosed and claimed herein may further comprise programmable means for releasing the clutch at a selected angle between the thigh frame and shank frame. When wearing the leg brace while ambulating, kinetic energy is converted into strain energy and stored in the spring during knee flexion. Thus, releasing the spring clutch during knee extension converts the stored energy back into kinetic energy and further provides support for the quadriceps muscle group in circumstances where one or more of the quadriceps muscles are weakened by, for example injury or nonuse.

The leg brace disclosed and claimed herein may comprise a one-way clutch in the knee assembly, configured to have an orientation selected such that its free direction of rotation occurs during the wearer's knee flexion.

The leg brace disclosed and claimed herein may further comprise means for programming the maximum permitted tibiofemoral joint forces during knee flexion.

The leg brace disclosed and claimed herein may further comprise a command module in wired or wireless communication with the programmable means for engaging the clutch at the selected angle.

The leg brace disclosed and claimed herein may further comprise automatic means for adjusting the selected angle, wherein the clutch is engaged, during an extended period of ambulation. This may be useful, for example, in the training or therapy of the braced leg.

The leg brace disclosed and claimed herein may further comprise programmable means for situationally adjusting the selected angle wherein the clutch is engaged. Such a program may be used, for example, in accordance with leg strength training goals.

The leg brace of claim 1, further comprising automatic means for adjusting the selected angle wherein the clutch is engaged, in accordance with usage history. In this circumstance, for example, the controller may be programmed to increase the selected angle wherein the clutch is engaged in order to require more quadriceps involvement and less assistance from the brace.

DETAILED DESCRIPTION OF THE DRAWINGS

Figure 1:
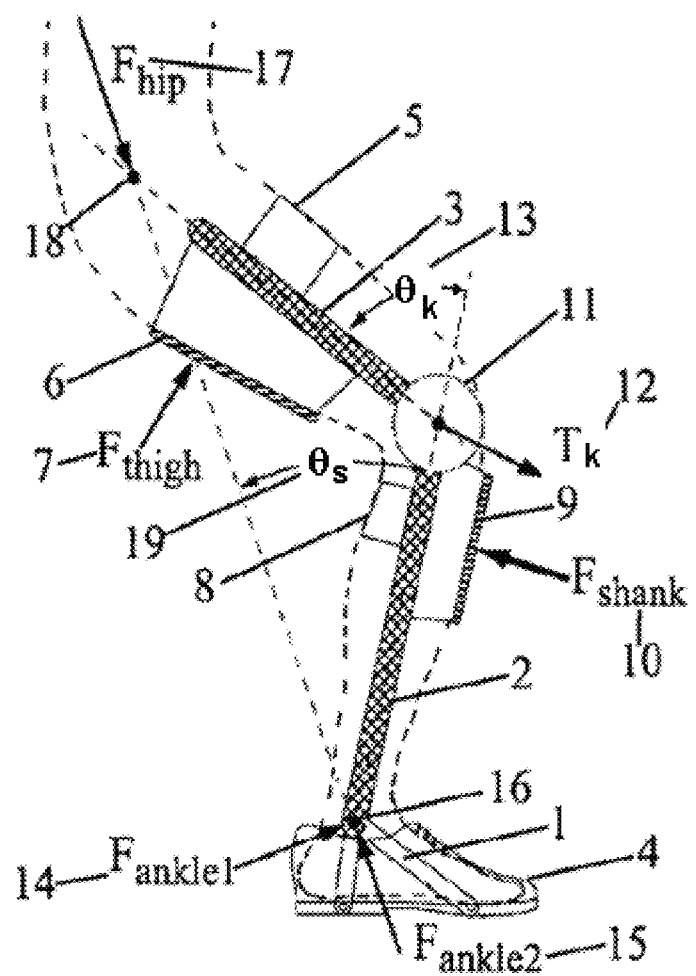
FIG. 1 shows a side view of a person wearing an embodiment of the present invention.

FIG. 1 shows a schematic side view of a person wearing one embodiment of the present invention. The general brace includes a shank frame 2, a thigh frame 3 and a knee assembly rotatably coupling the thigh frame to the shank frame 11 wherein is mounted a nonlinear torsion spring assembly, discussed infra. An alternate embodiment includes a shoe component 1 attached to the shank frame 2 for attaching to a wearer's shoe 4. Not shown are sensors for measuring the pressure and weight on the heel and other points on the bottom of the foot. Thigh frame 3 includes a thigh strap 5 and a padded thigh shell 6 for providing a means for coupling the force on the back of the thigh, $F_{thigh}$, 7 between the wearer's femur and the thigh frame 3. The shank frame 2 includes a shank strap 8 and a padded shank shell 9 for providing a means for coupling force at the front of the shank, $F_{shank}$ 10 between the wearer's tibia and the shank frame 2.

The knee assembly rotatably coupling the thigh frame to the shank frame 11 includes a spring (not shown) that, when compressed, produces a torque, $T_k$ 12 between the thigh frame 3 and the shank frame 2. The magnitude of $T_k$ 12 is dependent on the compression angle of the spring $\sigma_k - \sigma_e$, where $\sigma_e$ (not shown) is the selected knee angle at which the spring is engaged. The knee angle $\sigma_k$ shown at 13. Forces $F_{ankle1}$ 14 and $F_{ankle2}$ 15 are forces applied by the shoe component attached to the shank frame 1 to the shank frame 2 at an ankle joint 16. $F_{hip}$ 17 is a force applied by the torso to the hip socket caused by the gravitational field and inertial forces. Accordingly, as an approximation, $F_{hip}$ 17 has a direction pointing directly from hip socket 18 to ankle joint 16. The only direct coupling between ground reaction force (GRF) and the wearer's hip socket 18 is through the wearer's foot, tibia and femur. The brace, however, provides an indirect coupling assistance force $F_s$ between the GRF and the wearer's hip socket 18, pointing directly from ankle joint 16 to hip socket 18, with magnitude that increases from zero to its maximum value as a function of the knee angle $\sigma_k$ 13.

Figure 2:
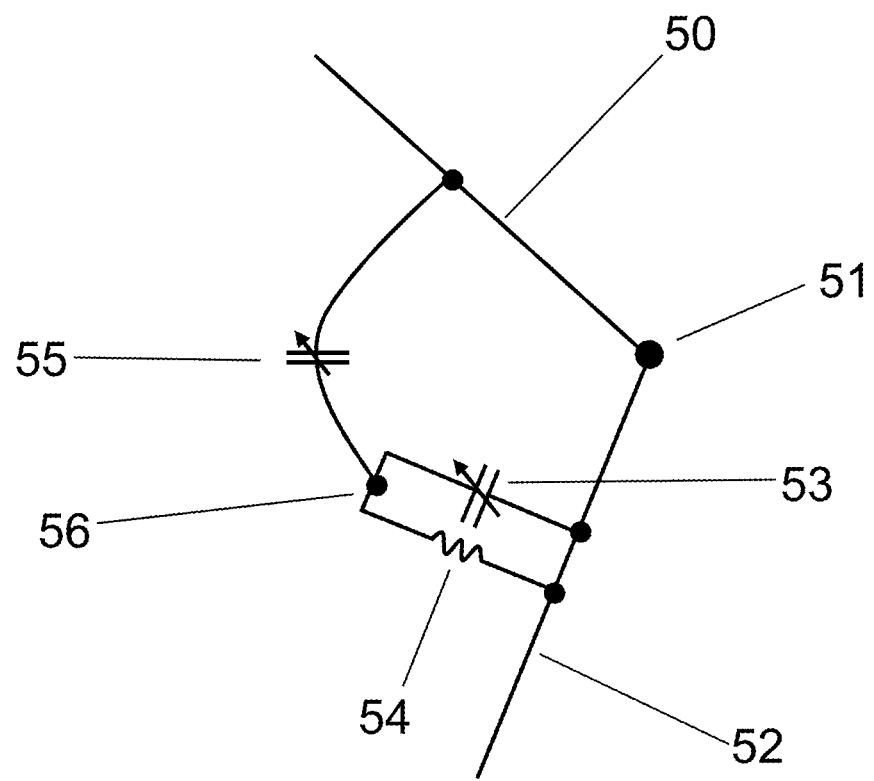
FIG. 2 shows a mechanical schematic diagram of the mechanical portion of the present invention.

FIG. 2 shows a mechanical schematic diagram of the knee assembly. One or more knee assemblies 51 and 53-55 rotatably couples the thigh frame 50, and shank frame 52. A hinge 51 is operatively coupled to a spring 54, which is controlled by an inner spring clutch 53 and an outer clutch 55. The spring 54, the inner spring clutch 53 and the outer clutch 55 are shown in operable contact with a drum 56. It should be understood that a brace as described herein may comprise one or more knee assemblies, for example, on the medial or lateral sides of the knee.

Figure 3:
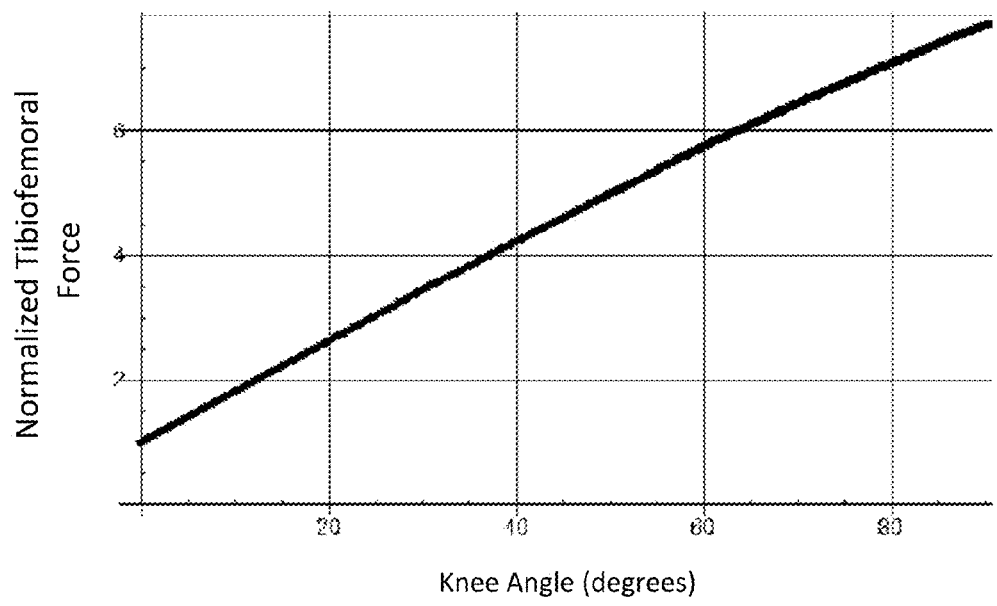
FIG. 3A shows the simulated normalized tibiofemoral joint force as a function of knee angle for an unassisted knee.
FIG. 3B shows simulated thigh assist force as a function of knee angle, delivered by an embodiment of this invention at seven assistance levels.
FIG. 3C shows simulated normalized tibiofemoral total force versus knee angle for seven levels of knee brace assistance.
Figure 3:
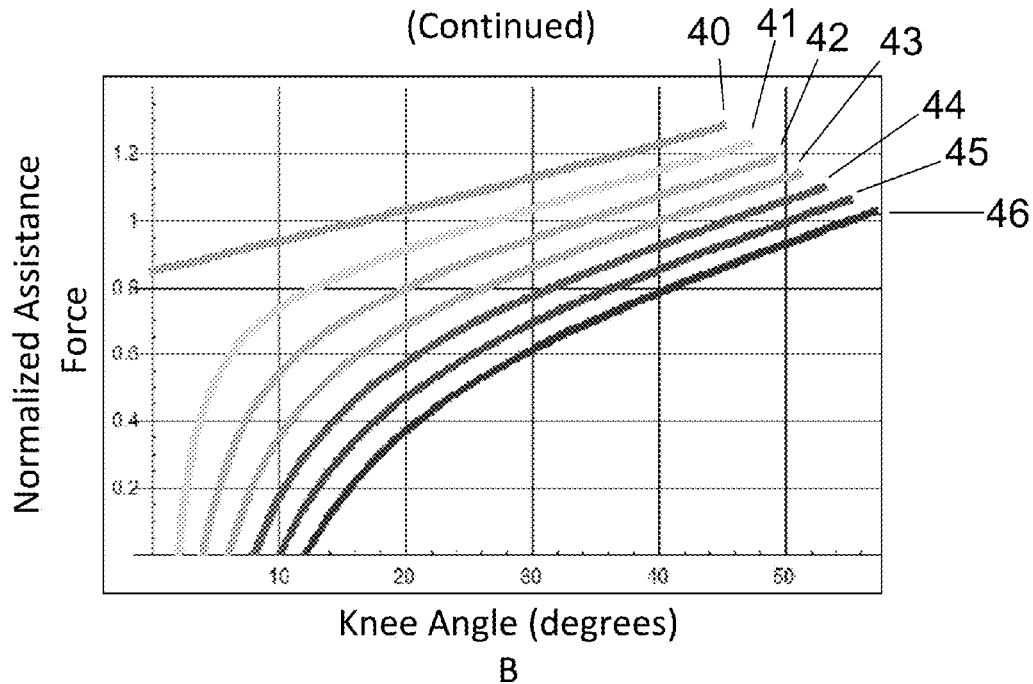
Figure 3:
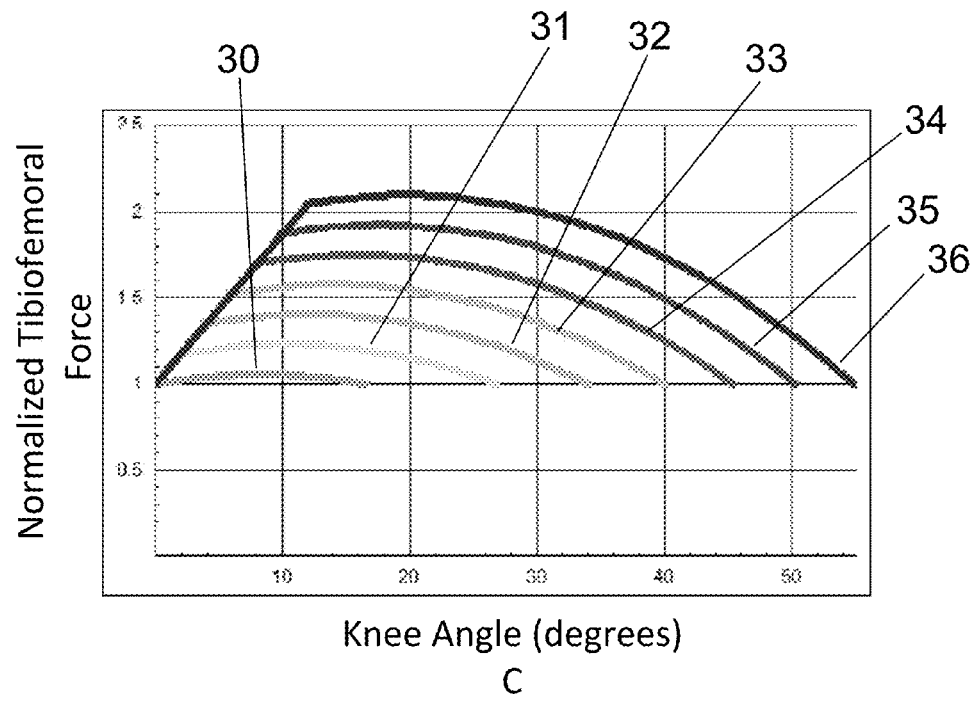

FIG. 3A shows the normalized tibiofemoral joint force versus knee angle (the angle between the thigh frame and the shank frame) for an unassisted leg assuming a constant patella tendon to knee axis separation distance. For the stance leg, the torque on the knee created by the torso weight plus swing leg has to equal the torque on the knee generated by the stance leg quadriceps muscle so that the normalized tibiofemoral force for the unassisted leg during the stance phase is given by:

$$F_{tf}(\vartheta_k) = 1 + \frac{L_{thigh}}{L_{pk}}\sin\left(\frac{\vartheta_k}{2}\right) \sim 1 + 10\sin\left(\frac{\vartheta_k}{2}\right)$$

Wherein $\sigma_k$ denotes the knee angle, $L_{thigh}$ denotes the length of the thigh, $L_{pk}$ denotes the patella tendon to knee axis separation distance, the length ratio is approximately equal to 10 and the actual force may be calculated by multiplying the normalized tibiofemoral joint force by the weight of the torso plus the weight of the swing leg.

A unity value on the Y scale represents approximately 83% of bodyweight (torso weight plus weight of swing leg). For a knee angle of zero, the normalized tibiofemoral force equals unity. As the knee angle increases, the tibiofemoral force increases approximately 10

$$\sin\left(\frac{\vartheta_k}{2}\right)$$

from unity to about six at a knee angle of 65°.

FIG. 3B shows plots of the simulated normalized assistance force (NAF) as a function of the angle between the thigh frame and the shank frame. Seven different curves corresponding to different angles of clutch engagement are shown at 2° increments 40-46. The curve labeled 40 is at the reference clutch engagement angle of 0°, wherein the maximum level of NAF is experienced by the user. Smaller levels of NAF are experienced by the user as the angle of clutch engagement is increased from 2° to 12° as shown in curves 41-46. For a particular nonlinear spring, the assistance force is given by:

$$F_s = \frac{\tau_s}{L_{thigh}\sin\left(\frac{\vartheta_k}{2}\right)} = \frac{[k_1(\vartheta_k - \vartheta_e)(1 + k_2(\vartheta_k - \vartheta_e))]}{L_{thigh}\sin\left(\frac{\vartheta_k}{2}\right)} = F_s(\vartheta_k - \vartheta_e)$$

Wherein the assistance force is computed as the ratio of the torque on the spring $\tau_s$ to the length of the thigh, $L_{thigh}$. The constants $k_1$ and $k_2$ may be obtained by fitting to the experimental data or by other equivalent means. The spring compression angle, denoted by $(\sigma_k - \sigma_e)$, is the difference between the knee angle, $\sigma_k$, and the angle at which the clutch engages, $\sigma_e$. The assistance force, $F_s(\sigma_k - \sigma_e)$, is thus a function of the spring compression angle. In the above, the function shown is not intended to be limiting but may take a number of reasonable forms, particularly if adjustable parameters are used. The function, $F_s(\sigma_k - \sigma_e)$, may be further interpolated and extrapolated using polynomials, spline functions, rational functions, normalized spectral elements and equivalents thereof or combinations thereof. Further, table lookup logic may comprise ordered table searching, searching with correlated values, estimation by neural networks, multidimensional estimation, equivalents thereof or combinations thereof.

FIG. 3C shows plots of the simulated normalized tibiofemoral force (NTF) as a function of the angle between the thigh frame and the shank frame for the assisted leg. Seven different curves corresponding to the angle of clutch engagement are shown at 2° increments 30-36. The curve labeled 30 is at the reference angle of 0°, wherein the minimum level of NTF is experienced by the user. This reference angle represents the maximum support from the brace (the maximum normalized assistance force (NAF)) when the clutch is engaged prior to or at heel strike. Greater levels of NTF are experienced by the user as the angle of clutch engagement is increased from 2° to 12° as shown in curves 31-36. In one embodiment, the assisted tibiofemoral force may be computed in the following way:

$$F_{tf}(\vartheta_k, \vartheta_e) = 1 + (1 - F_s(\vartheta_k - \vartheta_e))\sin\left(\frac{\vartheta_k}{2}\right) \text{ for } \vartheta_k \geq \vartheta_e \text{ and } F_s(\vartheta_k - \vartheta_e) < 1$$

Where $F_{tf}(\sigma_k, \sigma_e)$ is the normalized tibiofemoral force and $\sigma_k$, $\sigma_e$, $F_s(\sigma_k - \sigma_e)$, $L_{thigh}$, $L_{pk}$ are all as defined above. Without limitation, the condition $\sigma_k \geq \sigma_e$ may be applied optionally. However, it is also contemplated that support for knees in the hyperextended condition may require spring response that is defined for $\sigma_k \leq \sigma_e$. Moreover, the range of defined spring compression may vary. In one embodiment, the range through which spring compression is defined may be −10°-60°. In another embodiment, the range through which spring compression is defined may be −5°-50°. In still another embodiment, the range through which spring compression is defined may be 0°-45°. It may be convenient to define a "zero" of knee angle, $\sigma_k$, as a reference. This angle may be that at which the heel, the knee joint and the hip joint are all approximately collinear or at another angle of knee flexion.

Figure 4:
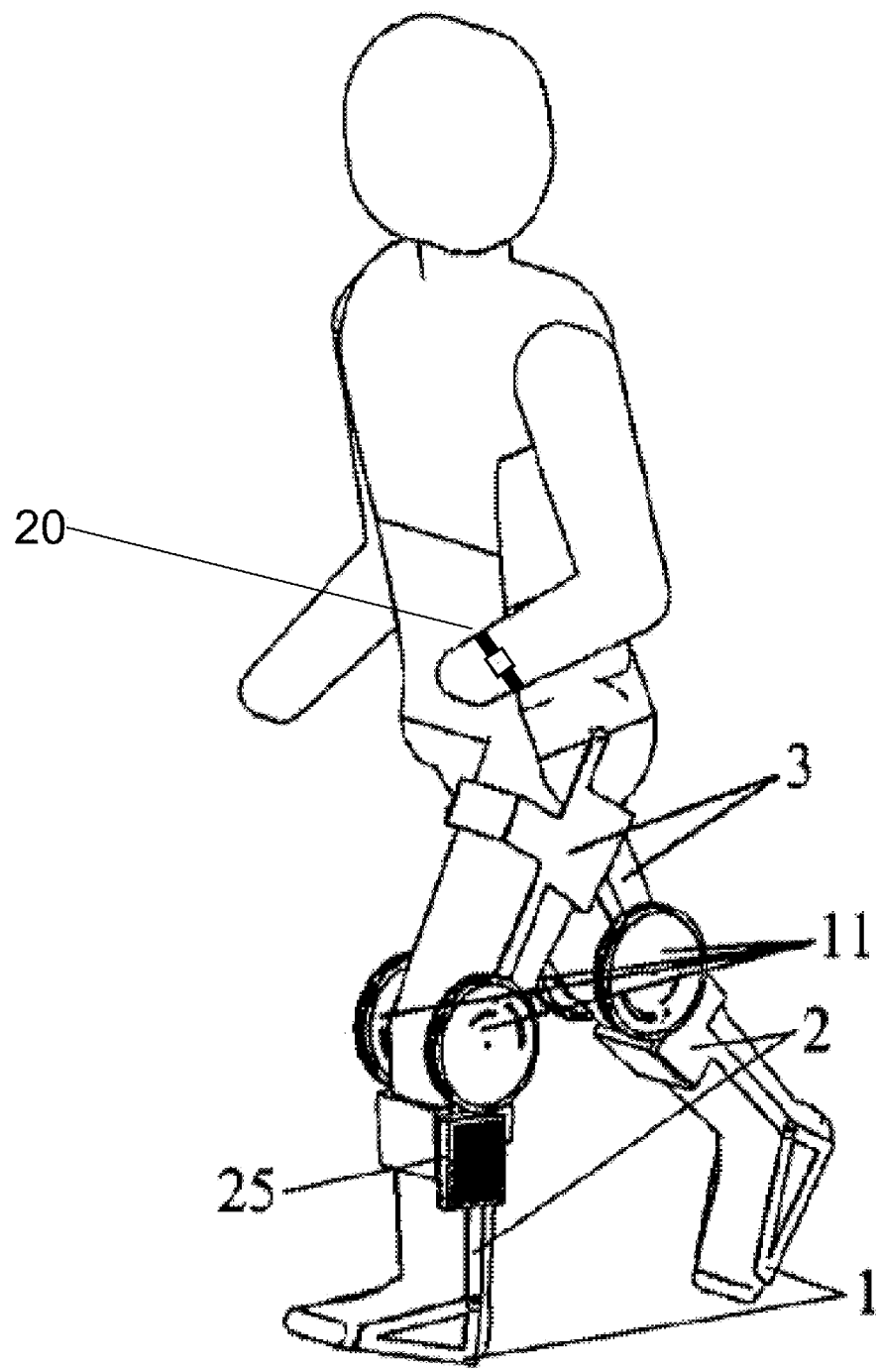
FIG. 4 shows a perspective view of a person employing the embodiment of FIG. 1 on both legs and a command module on the wrist.

FIG. 4 shows a perspective view of a person employing the embodiment of FIG. 1 on both legs. Each brace includes a shank frame 2, a shoe component attached to the shank frame 1, a thigh frame 3, at least one knee assembly rotatably coupling the thigh frame to the shank frame 11, and a control module 25, wherein are contained electronic components for the programmable means for engaging and releasing the clutch at selected angles as measured between the thigh frame and shank frame. Optionally, a command module 20 can be used in wired or wireless communication with the programmable means for engaging the clutch at the selected angle. The command module 20, may be used situationally to adjust settings. Shown in FIG. 4 are leg braces employing two knee assemblies for rotatably coupling the thigh frame to the shank frame, respectively on the lateral and medial sides of the knee. However, an embodiment of a brace having one knee assembly is also contemplated. Moreover, although a pair of braces is shown, it should be understood that a single brace on one leg can be employed.

Figure 5:
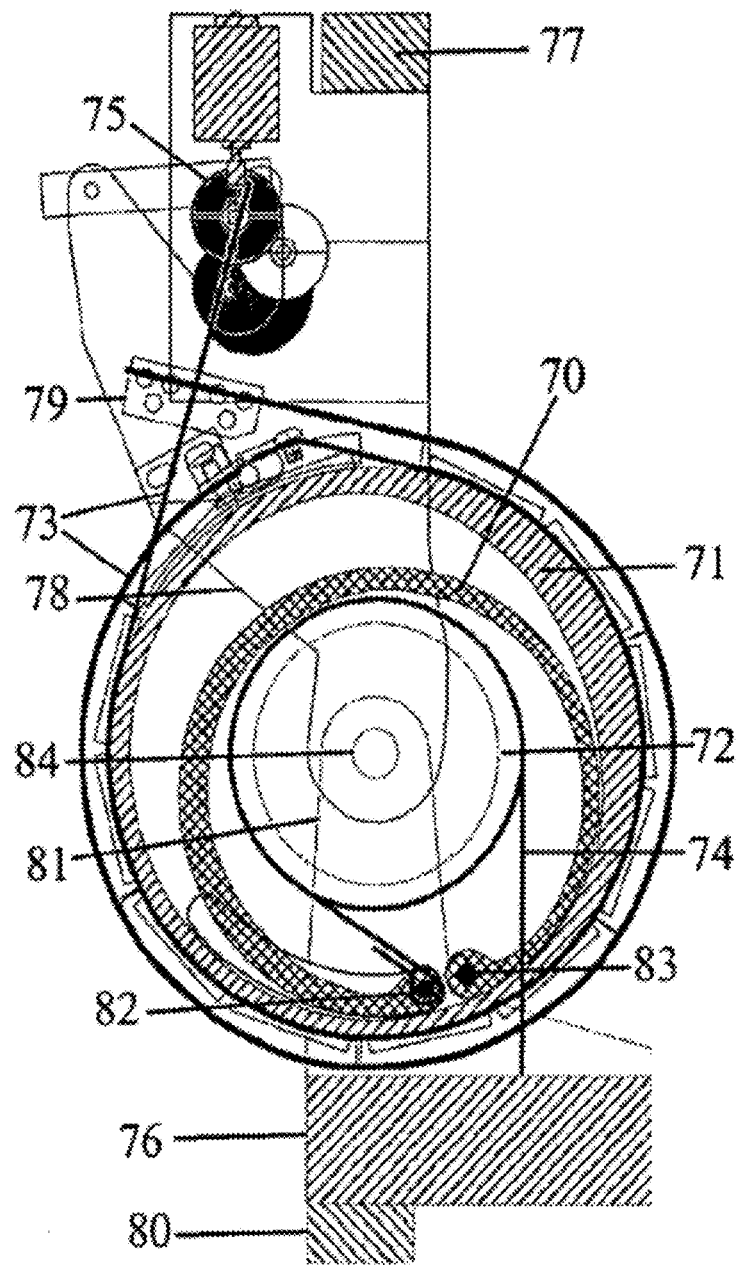
FIG. 5 shows a side view with a torsion spring and clutch.

FIG. 5 shows a side view of one embodiment of a knee assembly 11 (FIG. 1) coupled to the thigh frame 3 (FIG. 1) and the shank frame 2 (FIG. 1). The knee assembly 11 includes a thigh clutch assembly, a spring clutch assembly, a transfer arbor assembly, and a torsion spring 70. The thigh clutch assembly includes a thigh clutch wire 73 (at output arbor of the thigh clutch) and a thigh clutch actuator 75. The thigh clutch assembly is a mechanism for transferring torque from the thigh frame 3 (FIG. 1) to the transfer arbor under microprocessor control. The spring clutch assembly includes a spring clutch wire 74 (at output arbor of the spring clutch) and a spring clutch actuator 76. The spring clutch assembly is a mechanism for transferring torque from one arm of the torsion spring to its other arm under microprocessor control. The transfer arbor assembly includes two side plates (not shown), a thigh clutch arbor 71 (at input arbor of the thigh clutch), a spring clutch arbor 72 (at the input arbor of the spring clutch), and a transfer arbor pin 83. Knee axle 84 provides a means for the shank frame 2, thigh frame 3, and the transfer arbor to rotate around a single axis of rotation.

The thigh frame 3 includes a thigh frame side strut 77, a thigh frame side plate 78, and a thigh wire termination 79 that are fixed relative to one another. The shank frame 2 includes a shank frame side strut 80, a shank frame side plate 81, a torsion arm pin 82 that and are fixed relative to one another. One arm of the torsion spring is directly coupled to the shank frame 2 (FIG. 1) via the torsion arm pin 82 while the other arm of the torsion spring 70 is directly coupled to the thigh clutch arbor 71 via transfer arbor pin 83. The thigh frame 3, the shank frame 2, and the transfer arbor all rotate around a common axis of rotation. Stops prevent hyperextension of the knee joint and limit flexion of the knee to approximately 130°.

Figure 6:
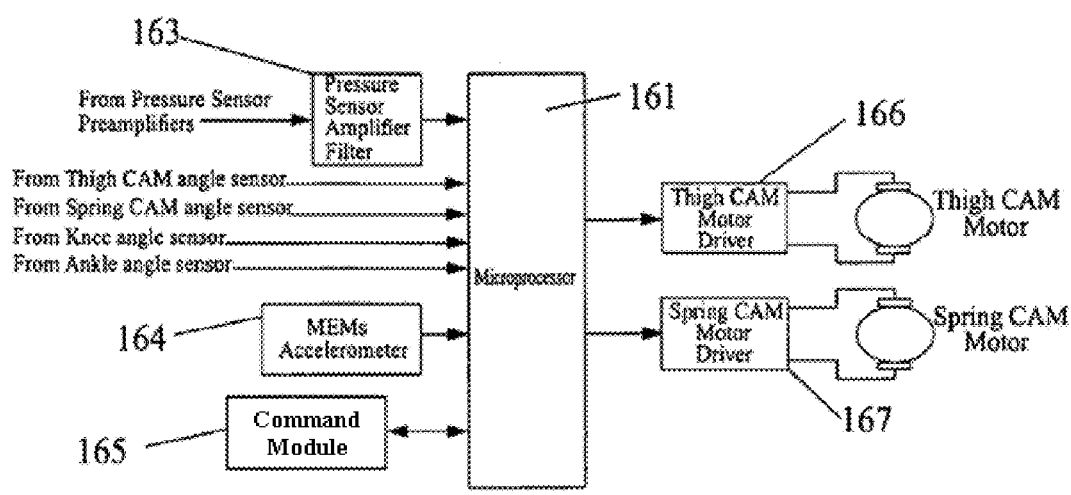
FIG. 6 is a block diagram showing an embodiment of an electronics control module.

Programmable means for engaging the clutch at the selected angle and releasing the clutch at the most propitious time may be provided in hardware, software or a combination. FIG. 6 is an embodiment of a block diagram of an electronics control module. Control of the brace is accomplished by a program resident within a microprocessor 161. The output voltages of four angle sensors are routed directly to A-D inputs of the microprocessor 161. The signals produced by three pressure pad preamplifiers within the brace (not shown), are amplified, rectified and filtered in pressure pad amplifier/filters 163. A dual axis accelerometer 164 allows measurement of the acceleration on the shank frame 2 (FIG. 1) over a selected acceleration range. An exemplary acceleration range is +/−2.0 G. Another exemplary acceleration range is +/−1.5 G. Still another exemplary acceleration range is +/−1.0 G. An exemplary tolerance for the measured acceleration is one part in 5000. A further exemplary tolerance for the measured acceleration is 1 part in 1000. A still further exemplary tolerance for the measured acceleration is one part in 500. The accelerometer is employed both to detect heel strike and to sense the shank frame 2 orientation relative to the earth's gravitational field. A command module 165 and 20 (FIG. 4) in wired or wireless communication with the programmable means for engaging the clutch at the selected angle allows the wearer to enter commands to the electronics module during configuration and situationally. A pulse width modulated (PWM) current limited thigh motor driver 166 is employed to drive the motor within the thigh clutch actuator 75 (FIG. 5). The driver provides a means for the microprocessor to drive the motor in both directions. A PWM current limited spring motor driver 167 is employed to drive the motor within the spring clutch actuator 76 (FIG. 5). The microprocessor 161 may also drive other devices such as LED indicator lights, one or more displays, speakers and the like. Further included but not shown may be a keyboard for local programming, communication equipment for remote programming and telemetric monitoring and memory storage for storing the usage data for later analysis and programs for training exercises, adjusting the brace for extended periods of ambulation and adjusting the brace for other situations encountered during use.

Wired communication may be accomplished via digital or analog methods in a variety of serial or parallel formats. Wireless communication may be accomplished via Bluetooth, WiFi, infrared signals or the equivalent. Such commands can be issued from a wrist module 20, a sequence of pressures applied to the pressure pads in a sensorized shoe insole, a keyboard, or biometric indicators such as voice, eye movement, finger arm or wrist movement, equivalents thereof or combinations thereof.

In this embodiment, a pulse width modulated (PWM) current limited thigh CAM motor driver 166 is employed to drive the motor within the thigh clutch actuator 75 (FIG. 5). The driver provides a means for the microprocessor to drive the motor in both directions. A PWM current limited spring CAM motor driver 167 is employed to drive the motor within the spring clutch actuator 76 (FIG. 5). The microprocessor 161 may also drive other indicators such as LEDs, displays, speakers, wireless devices such as Bluetooth, WiFi, infrared or the equivalent. In this embodiment uses two motor/gearbox driven CAMs 166 and 167 to supply a force to the control side of each of the clutches. In normal operation, the CAM makes one revolution for each step cycle. The control CAM has an engineered shape such that the control force can be varied from zero to maximum over any time period and the force can be changed from maximum to zero almost instantaneously. The shape of the CAM may further be designed to minimize the power drain from the battery.

Figure 7:
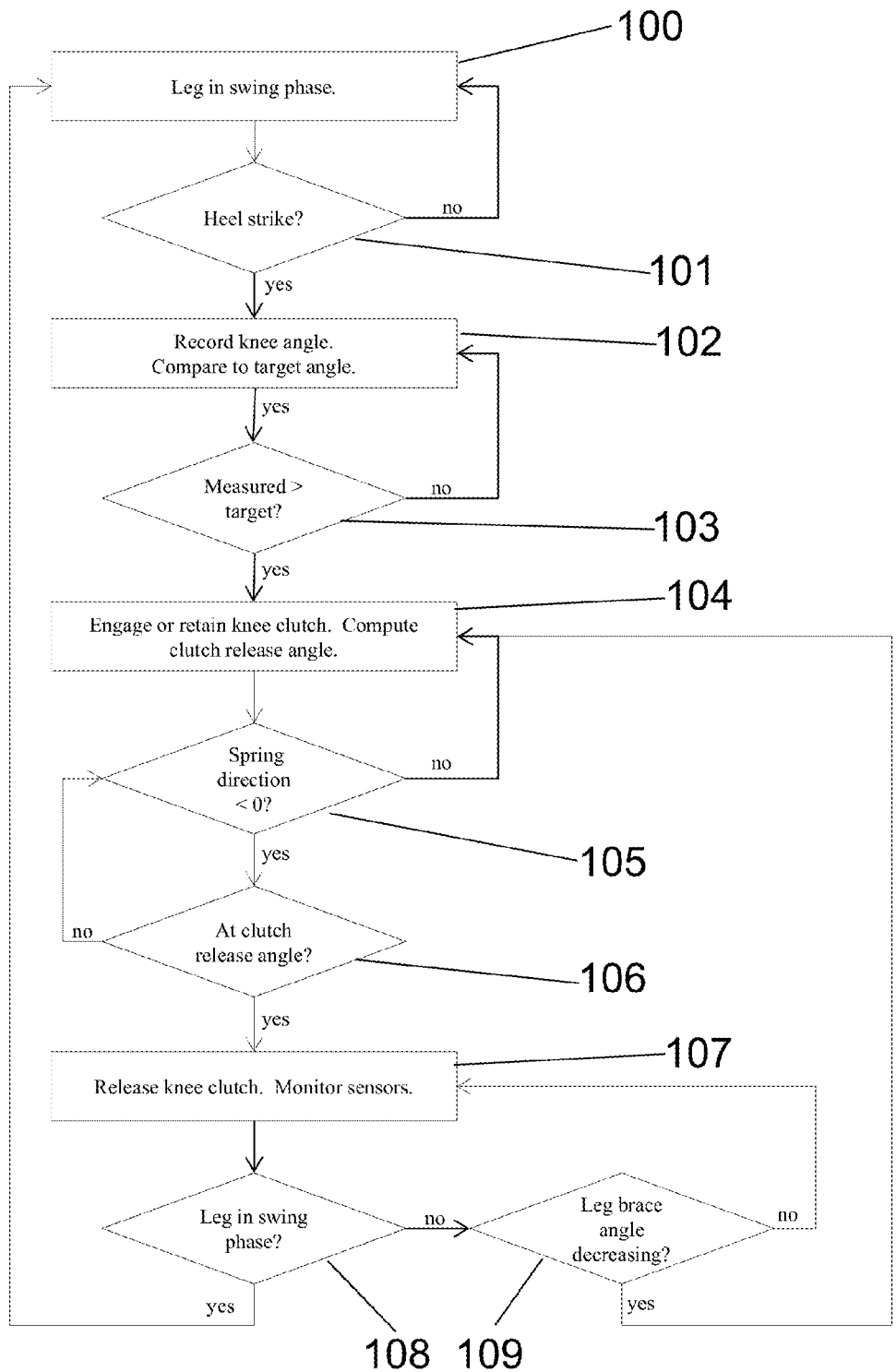
FIG. 7 is a block diagram of an embodiment of control logic that may be implemented in the electronics control module.

FIG. 7 shows a diagram of the control logic used to select the angle of clutch engagement and release and to actuate and release a clutch. In this embodiment, it is assumed for simplicity that status monitoring is done continually and that monitored parameter information is fetched or otherwise made available when required. Further, for simplicity, it is assumed that redundant commands are ignored. For example, a command to release an already released clutch is ignored. Further, it is understood herein that collinear control lines are presumed to function independently.

As shown in FIG. 7, at some point during ambulation, the leg is in its swing phase, as depicted in control module 100, wherein the knee joint is being extended and the knee clutch is disengaged. There is negligible pressure on the bottom of the foot, the spring is not compressed and the spring compression angle is defined as zero under this condition. During the swing phase, heel forces are monitored to determine whether heel strike has occurred as shown in decision point 101. In this embodiment, the system is looped between control module 100 and decision point 101 until heel strike occurs.

Heel strike is detected by pressure sensors at the bottom of the foot 163 (FIG. 6) Heel strike is confirmed by accelerometer 164 (FIG. 6) and/or a tilt sensor (not shown) and control is passed to status block 102 where the knee angle (the angle between the shaft frame and thigh frame) is measured and tested at decision point 103 to determine whether the target angle for clutch engagement has been reached. During knee flexion, tibiofemoral forces increase as torso weight is shifted onto the braced leg. Pressure sensors on the sole of the foot measure the pressure as the knee undergoes flexion. Once the target angle is reached, control is passed to routine 104, which issues a command to engage the knee clutch.

Control is then passed to decision point 105, which tests whether the spring is compressing (increasing spring angle) or is decompressing (decreasing spring angle). Increases in the tibiofemoral force are limited by further compression of the spring as weight continues to be shifted onto the brace. If the spring angle rate of change is positive, the knee clutch remains engaged; control returns to 104 which passes control to decision point 105. If the spring angle rate of change is negative, control is passed to decision point 106 which tests whether the knee angle has reached its prescribed value for clutch release e.g. the spring compression angle has reached a value of zero.

Control is looped between decision points 105 and 106 until the prescribed clutch release knee angle is reached. Once the release angle is reached, control is passed to control module 107 which releases the knee clutch, allowing the knee to rotate freely.

Control is then passed to decision point 108, which tests continually whether the leg is in swing phase. If the leg is in swing phase, control is passed to control module 100. If the leg is not in swing phase, control is passed to decision point 109, which tests whether the angle between the thigh frame and the shank frame is decreasing with time. If the leg brace angle is decreasing, control is passed to control module 104, which engages the knee clutch and computes or obtains from memory the clutch release angle. If the leg brace angle is increasing or stationary, control is passed to control module 107.

It should be understood that status monitoring and control of parameters such as angles, forces, for example at heel strike, spring direction, and rates of change may be accomplished in-line or continually by means of interrupt service routines, direct memory access, adaptive interrupt systems, multiprocessor environments and the like. Further, interrupts and direct memory access events can be masked and/or prioritized when required. Communication with the processor can be accomplished by various means known in the art, for example, parallel communication, serial communication, communication via a universal serial bus, firewire and the like. Further, various wireless technologies may be employed such as WiFi, ZigBee, infrared, Bluetooth and the like. Communication methods can be point-to-point or broadcast to all points, wherein, at each point of contact, irrelevant signals are discarded.

Different types of clutch may be used. Without limitation, these can include centrifugal clutches, cone clutches, torque limiting clutches, hydraulic clutches, electromagnetic clutches, freewheel clutches, ratchet clutches wrap spring clutches and the like. Further, clutches employed as described herein may be one-way clutches. One-way clutches transmit torque in one rotational direction while stopping torque in the opposite direction. In one embodiment, both a microprocessor activated thigh clutch and spring clutch are used during normal operation. Both clutches are one-way dual-state clutches. In many embodiments, there is an input arbor and an output arbor and a means for coupling torque between input arbor and output arbor. In dual-state clutches, there are two states in which the clutch is either released or actuated. In its released state, negligible torque is transferred from the input arbor to the output arbor before slippage occurs. In the actuated state, a large torque is coupled from input arbor to output arbor before slippage occurs. Transition between states may be effected either mechanically or electrically typically via a solenoid.

Operation of a one-way dual-state clutch (employed in an embodiment of the invention) is similar to a dual-state clutch in the released state. In the actuated state, operation of the one-way dual-state clutch differs because large amounts of torque can be transferred from input arbor to output arbor only in one rotational direction, called the "hard" direction. When in the actuated state, only a small amount of torque is transferred from input arbor to output arbor before slippage occurs in the other direction, called the "easy" direction. Note that in any physical implementation of a one-way dual-state clutch, the maximum torque transferable between the input arbor and the output arbor without slippage is limited by the physical parameters of the clutch. Moreover, the easy direction torque will normally be much larger than release state transfer torque.

In accordance with the above referenced drawings and the accompanying description, means for engaging the clutch may comprise an assembly of pressure sensors, angle sensors, one or more accelerometers, actuators processors, auxiliary circuits, program logic, equivalents thereof or combinations thereof.

In accordance with the above referenced drawings and the accompanying description, programmable means for engaging the clutch at a selected angle between the thigh frame and shank frame may comprise an assembly of pressure sensors, angle sensors, one or more accelerometers, actuators processors, auxiliary circuits, program logic, equivalents thereof or combinations thereof.

In accordance with the above referenced drawings and the accompanying description, programmable means for releasing the clutch at a selected angle between the thigh frame and shank frame may comprise an assembly of pressure sensors, angle sensors, one or more accelerometers, actuators processors, auxiliary circuits, program logic, equivalents thereof or combinations thereof.

In accordance with the above referenced drawings and the accompanying description, means for programming the maximum permitted tibiofemoral joint forces during knee flexion may comprise an assembly of pressure sensors, angle sensors, one or more accelerometers, actuators processors, auxiliary circuits, table lookup logic, program logic, equivalents thereof or combinations thereof. For example, in circumstances where the user can tolerate a tibiofemoral force corresponding to a normalized value of 1.6, the microprocessor of FIG. 6 may be programmed to provide more assistance from the leg brace by adjusting the angle of clutch engagement to occur at about 6°. If even more support is required, the angle of clutch engagement can occur at 0° (heel-strike), so that the maximum normalized tibiofemoral force reaches a value of only about 1.1. Angle values can be incorporated into program logic by using any of the methods of interfacing discussed herein.

In accordance with the above referenced drawings and the accompanying description, automatic means for adjusting the selected angle wherein the clutch is engaged, during an extended period of ambulation may comprise an assembly of pressure sensors, angle sensors, one or more accelerometers, actuators processors, auxiliary circuits, table lookup logic, program logic, equivalents thereof or combinations thereof. For example, in circumstances where the user experiences fatigue during ambulation, the microprocessor of FIG. 6 may be programmed to provide more assistance from the leg brace by incrementally providing more support to the tibiofemoral joint by incrementally decreasing the angle at which the clutch is engaged over the course of the walk, in accordance with FIG. 3C. If clutch engagement occurs at an angle of 12°, for example, the maximum normalized tibiofemoral force reaches a value of about 2.1. If clutch engagement occurs at an angle of 6°, the maximum normalized tibiofemoral force reaches a value of about 1.6. On the other hand, if clutch engagement occurs at an angle of 0° (heel-strike), the maximum normalized tibiofemoral force reaches a value of only about 1.1 as the brace supplies more stored energy from the spring. Angle values can be incorporated into program logic by using any of the methods of interfacing discussed herein.

In accordance with the above referenced drawings and the accompanying description, means for situationally adjusting the selected angle wherein the clutch is engaged, may comprise an assembly of pressure sensors, angle sensors, one or more accelerometers, actuators processors, auxiliary circuits, table lookup logic, program logic, a command module carried or worn by the user, equivalents thereof or combinations thereof. The command module may be configured to monitor various bodily functions such as electrocardiogram signals heart rate, perspiration, body temperature, blood pressure, oxygen level and the like. A wired or wireless communications module can be used to program the microprocessor of FIG. 6 to reduce the exertion of the muscles in the braced leg upon command. For example, in circumstances where measurements indicate a low blood oxygen level, the microprocessor of FIG. 6 may be programmed to provide more assistance from the leg brace by decreasing the angle at which the clutch is engaged, in accordance with FIG. 3C. In this example, if clutch engagement occurs at an angle of 6°, the maximum normalized tibiofemoral force reaches a value of about 1.6. In response to a lower oxygen level, the, clutch engagement could be reduced to an angle of 0° (heel-strike), the maximum normalized tibiofemoral force reaches a value of only about 1.1 as the brace supplies more stored energy from the spring. In addition, quadriceps involvement during the swing phase decreases to a negligible value. Clutch engagement angle values can be programmed situationally as inputs to the controlling program logic by using any of the methods of interfacing discussed herein.

In accordance with the above referenced drawings and the accompanying description, automatic means for adjusting the selected angle at which the clutch is engaged in accordance with a training schedule may comprise an assembly of pressure sensors, angle sensors, one or more accelerometers, actuators processors, auxiliary circuits, table lookup logic, program logic, a command module carried or worn by the user, equivalents thereof or combinations thereof. In addition, a training schedule can be incorporated into the microprocessor so that the angle of clutch engagement is varied in accordance with the amount of tibiofemoral force and quadriceps involvement. The training module can be programmed to increase the angle of clutch engagement over days, weeks or months or the angle of clutch engagement can be varied according to whether certain physiological targets are achieved. The command module may be configured to monitor various physiological parameters such as electrocardiogram signals heart rate, perspiration, body temperature, blood pressure, oxygen level and the like. A wireless communications module, such as a Zigbee radio module, can be used to program the microprocessor of FIG. 6 to change the exertion of the muscles in the braced leg upon command. For example, in circumstances where a target heart rate is desired, the microprocessor of FIG. 6 may be programmed to provide less assistance from the leg brace by increasing the angle at which the clutch is engaged, and then provide a level of assistance designed to maintain the desired heart rate by decreasing or increasing the angle as required to maintain the desired heart rate. The level of assistance from the brace can thus be adjusted upward or downward by adjusting the clutch engagement angle. Clutch engagement angle values can programmed situationally as inputs to the controlling program logic by using any of the methods of interfacing discussed herein.

Pressure sensors may comprise piezoelectric sensors, piezoresistive sensors, capacitive sensors, which may comprise foams or other elastic materials as well as ceramics and fluids, electromagnetic sensors, in which the physical displacement of a diaphragm or cantilever causes changes in inductance, reluctance or capacitance, a linear variable differential transformer device, Hall effect device, equivalents thereof or combinations thereof.

Angle sensors may comprise accelerometers, liquid capacitive inclinometers, electrolytic inclinometers, gas bubble in liquid devices, pendulum devices, giant magnetoresistive sensors, potentiometric sensors, Hall effect sensors, anisotropic magnetoresistive sensors, optical encoders, equivalents thereof or combinations thereof.

Accelerometers may comprise piezoresistive sensors, piezoelectric sensors, moving mass sensors, giant magnetoresistive sensors, anisotropic magnetoresistive sensors, capacitive sensors, resonant beam sensors, vibrating cantilever sensors, force balance sensors, transducer electronic data sheet (TEDS) accelerometers, wireless accelerometers, equivalents thereof or combinations thereof. Accelerometers may operate in uniaxial, biaxial or triaxial mode.

Actuators may comprise optoelectronic devices, CAM devices, linear motors, voice coils, moving magnetic actuators, amplified and direct piezoelectric devices, electric motors, pneumatic actuators, hydraulic pistons, relays, comb drive devices, thermal bimorphs, digital micromirror devices, electroactive polymers, screw jack, ball screw and roller screw actuators, hoist, winch, rack and pinion, chain drive, belt drive, rigid chain and rigid belt actuators, gear drive actuators, equivalents thereof or combinations thereof.

The sensors and actuators described above may be manufactured as microelectronic nanoelectronic or microelectromechanical devices, equivalents thereof or combinations thereof.

Processors may comprise any circuit for performing data processing, including digital signal processors, single processors, parallel processors, analog processors, memory management processors, optical processors, equivalents thereof and combinations thereof. In addition, processors may include auxiliary circuits, either integrated with the processor or in separate devices operating with the processor. Auxiliary circuits may be any circuit that provides an additional function on behalf of the processors and can be shared between two or more processors. Auxiliary circuits may include memories such as semiconductor memories, magnetoresistive memories, disk memories, flash memories, or any equivalent means for storing data, auxiliary circuits may further comprise gate arrays, adders, other programmed logic circuits, amplifiers, triggers, A/D converters, D/A converters, optical interfaces, serial and parallel interfaces, buffers, masking circuits, encryption circuits, direct memory access circuits, equivalents thereof or combinations thereof.

Program logic may comprise computer programs written in any known language, such as C, C++, Pearl, Fortran, Basic, Pascal, assembly language, machine language, equivalents thereof or combinations thereof. Program logic may further comprise parallel processing logic for employing multiple processors or processor cores, direct memory access logic for continual monitoring functionality, masked direct memory access, interrupt routines, interrupt service routines, equivalents thereof or combinations thereof.

Table lookup logic may comprise interpolation and extrapolation routines, based on polynomials, spline functions, rational functions, normalized spectral elements, equivalents thereof or combinations thereof. Further, table lookup logic may comprise ordered table searching, searching with correlated values, estimation by neural networks, multidimensional estimation, equivalents thereof or combinations thereof. Data for table lookup may be obtained experimentally, using the brace and electronics described herein. Further, data such as that shown in FIG. 3C may be obtained by simulation that incorporates the biomechanics of the braced leg in accordance with the forces and angles depicted in FIG. 1.

Although the present invention has been shown and described with reference to particular examples, various changes and modifications which are obvious to persons of ordinary skill in the art to which the invention pertains are deemed to lie within the spirit, scope and contemplation of the subject matter as set forth in the appended claims.

What is claimed is:

1. An improved leg brace having a thigh frame, a shank frame, a knee assembly rotatably coupling the thigh frame to the shank frame, and a shoe component attached to the shank frame; the knee assembly having a spring, clutch, operatively coupled to the spring; and programmable means for engaging the clutch at a selected angle between the thigh frame and shank frame, wherein the spring delivers is an assistance force when the clutch is engaged at the selected angle between the thigh frame and shank frame.

2. The leg brace of claim 1, further comprising: a second knee assembly configured so that, when in use, one knee assembly is on the medial side of the leg and the other knee assembly is on the lateral side of the leg.

3. The leg brace of claim 1, further comprising: programmable means for releasing the clutch at a selected angle between the thigh frame and shank frame.

4. The leg brace of claim 1, wherein the clutch is a one-way clutch.

5. The leg brace of claim 1, further comprising means for programming the maximum permitted tibiofemoral joint forces during knee flexion.

6. The leg brace of claim 1, further comprising a command module in wired or wireless communication with the programmable means for engaging the clutch at the selected angle.

7. The leg brace of claim 1, further comprising automatic means for adjusting the selected angle wherein the clutch is engaged, during an extended period of ambulation.

8. The leg brace of claim 1, further comprising programmable means for situationally adjusting the selected angle wherein the clutch is engaged.

9. The leg brace of claim 1, further comprising automatic means for adjusting the selected angle at which the clutch is engaged in accordance with a training schedule.

10. A leg brace, comprising:
   a. a shank frame;
   b. a thigh frame;
   c. at least one knee joint, rotatably coupling the shank frame to the thigh frame;
   d. at least one non-linear torsion spring having a torsional axis at the at least one knee joint wherein the torsion spring hardens with increasing angle of knee flexion;

e. at least one clutch with an input arbor coupled to the at least one non-linear torsion spring and an output arbor coupled to:
   i. the thigh frame; or
   ii. the shank frame;
f. a programmable controller, operatively coupled to the at least one clutch, for:
   i. engaging the at least one clutch at a selected angle between the thigh frame and the shank frame in relation to heel strike during ambulation; and
   ii. releasing the at least one clutch at a selected angle between the thigh frame and the shank frame during knee extension,
wherein the at least one non-linear torsion spring is delivers an assistance force when the clutch is engaged at the selected angle between the thigh frame and shank frame.

11. The leg brace of claim 10, further comprising a command module, in wired or wireless communication with the programmable controller, for situationally selecting the angle of knee flexion at which the at least one clutch is engaged.

12. The leg brace of claim 10, wherein the at least one clutch is a one-way clutch.

13. The leg brace of claim 10, further comprising automatic means for adjusting the selected angle wherein the clutch is engaged, during an extended period of ambulation.

14. The leg brace of claim 10, further comprising programmable means for situationally adjusting the selected angle wherein the clutch is engaged.

15. The leg brace of claim 10, further comprising automatic means for adjusting the selected angle at which the clutch is engaged in accordance with a training schedule.

* * * * *